US011234667B2

(12) United States Patent
Andreyev et al.

(10) Patent No.: US 11,234,667 B2
(45) Date of Patent: Feb. 1, 2022

(54) SCATTER CORRECTION USING EMISSION IMAGE ESTIMATE RECONSTRUCTED FROM NARROW ENERGY WINDOW COUNTS IN POSITRON EMISSION TOMOGRAPHY

(71) Applicant: KONINKLIJKE PHILIPS N.V., Eindhoven (NL)

(72) Inventors: Andriy Andreyev, Willoughby Hills, OH (US); Xiyun Song, Cupertino, CA (US); Jinghan Ye, Livermore, CA (US); Chuanyong Bai, Solon, OH (US); Zhiqiang Hu, Twinsburg, OH (US); Douglas B. McKnight, Chardon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 134 days.

(21) Appl. No.: 16/647,326

(22) PCT Filed: Aug. 30, 2018

(86) PCT No.: PCT/EP2018/073293
§ 371 (c)(1),
(2) Date: Mar. 13, 2020

(87) PCT Pub. No.: WO2019/052816
PCT Pub. Date: Mar. 21, 2019

(65) Prior Publication Data
US 2021/0030387 A1 Feb. 4, 2021

Related U.S. Application Data

(60) Provisional application No. 62/558,389, filed on Sep. 14, 2017.

(51) Int. Cl.
*A61B 6/00* (2006.01)
*G16H 30/20* (2018.01)
(Continued)

(52) U.S. Cl.
CPC ............ *A61B 6/5282* (2013.01); *A61B 6/037* (2013.01); *A61B 6/461* (2013.01); *G06T 11/005* (2013.01); *G16H 30/20* (2018.01)

(58) Field of Classification Search
None
See application file for complete search history.

(56) References Cited

U.S. PATENT DOCUMENTS 9,535,175 B2 1/2017 Laurence
9,600,910 B2 3/2017 Wang
(Continued)

FOREIGN PATENT DOCUMENTS

WO 2013175352 A1 11/2013

OTHER PUBLICATIONS

Ferreira, N.C. et al "A Hybrid Scatter Correction for 3D PET based on an Estimation of the Distribution of Unscattered Coincidences: Implementation on the ECAT EXACT HR+", Physics in Medicine and Biology IOP Publishing UK, vol. 47, No. 9, May 2002, pp. 1555-1571.

Popescu, L.M. et al "PET Energy-Based Scatter Estimation and Image Reconstruction with Energy-Dependent Corrections; Energy-based Scatter Estimation and Image Reconstruction for PET", Physics in Medicine and Biology, vol. 51, No. 11, Jun. 2006, pp. 2929-2937.

(Continued)

*Primary Examiner* — Hoon K Song

(57) ABSTRACT

A non-transitory storage medium storing instructions readable and executable by an imaging workstation (18) including at least one electronic processor (20) to perform an image reconstruction method (100). The method includes: receiving emission imaging data (22) from an image acquisition device (12) wherein the emission imaging data has been filtered using an acquisition energy passband (18); generating filtered imaging data by filtering the emission
(Continued)

imaging data with a second energy passband (90) that is narrower than an acquisition energy passband; reconstructing the filtered imaging data to generate an intermediate image; estimating one or more scatter correction factors (SCFs) from the intermediate image; and reconstructing the emission imaging data corrected with the estimated SCFs to generate a reconstructed image.

25 Claims, 3 Drawing Sheets

(51) Int. Cl.
*A61B 6/03* (2006.01)
*G06T 11/00* (2006.01)

(56) References Cited

U.S. PATENT DOCUMENTS

| 2017/0103551 | A1* | 4/2017 | Sun | G06T 11/005 |
| 2018/0114346 | A1* | 4/2018 | Sun | G01S 7/4866 |
| 2018/0203140 | A1* | 7/2018 | Miao | G01T 1/2985 |
| 2020/0170605 | A1* | 6/2020 | Qi | G01T 1/2985 |

OTHER PUBLICATIONS

Herraiz, J.L. et al. "Sensitivity Estimation in Time-of-Flight List-Mode Positron Emission Tomography", Medical Physics, vol. 42, No. 11, Nov. 2015, pp. 6690-6702.
International Search Report and Written Opinion of PCT/EP2018/073293, dated Nov. 23, 2018.

* cited by examiner

SCATTER CORRECTION USING EMISSION IMAGE ESTIMATE RECONSTRUCTED FROM NARROW ENERGY WINDOW COUNTS IN POSITRON EMISSION TOMOGRAPHY

Cross-Reference to Prior Applications

This application is the U.S. National Phase application under 35 U.S.C. § 371 of International Application No. PCT/EP2018/073293, filed on Aug. 30, 2018, which claims the benefit of U.S. Provisional Patent Application No. 62/558,389, filed on Sep. 14, 2017. These applications are hereby incorporated by reference herein.

FIELD

The following relates generally to the medical imaging arts, medical image interpretation arts, image reconstruction arts, and related arts.

BACKGROUND

Compton scatter is a major image quality and quantitation degradation factor in positron emission tomography (PET) that should be accounted for during high quality image reconstruction. Accurate scatter correction in PET image reconstruction suffers from a "chicken-and-egg" problem. Scatter correction factors need to be simulated from an attenuation map and an emission map estimate. The problem is that, before scatter correction has been applied, the emission map estimate is contaminated with scatter. If such contaminated emission estimate is used for scatter correction, in the end the scatter correction factors would be biased.

In one approach for addressing this problem, an iterative approximation of emission estimate is used to minimize scatter. The iterative approach starts with an emission estimate (with scatter in general), uses it for scatter simulation, then uses the scatter estimate to reduce the scatter in the emission estimation, and then the process is iterated for a given number of iterations to obtain an emission estimate with acceptable level of remaining scatter. The iterative approach complicates the workflow and is time-consuming. In a variant approach, to compensate for this, the generation of emission estimate is done in coarse sinogram space and without time of flight (TOF) localization of events to save time, but with the price of compromised accuracy.

The following discloses new and improved systems and methods to overcome these problems.

SUMMARY

In one disclosed aspect, a non-transitory storage medium stores instructions readable and executable by an imaging workstation including at least one electronic processor to perform an image reconstruction method. The method includes: receiving emission imaging data from an image acquisition device wherein the emission imaging data has been filtered using an acquisition energy passband; generating filtered imaging data by filtering the emission imaging data with a second energy passband that is narrower than an acquisition energy passband; reconstructing the filtered imaging data to generate an intermediate image; estimating one or more scatter correction factors (SCFs) from the intermediate image; and reconstructing the emission imaging data corrected with the estimated SCFs to generate a reconstructed image.

In another disclosed aspect, an imaging system includes an image acquisition device. At least one electronic processor is programmed to: receive emission imaging data from the image acquisition device wherein the emission imaging data has been filtered using an acquisition energy passband; generate filtered imaging data by filtering the emission imaging data with a second energy passband that is narrower than an acquisition energy passband; reconstruct the filtered imaging data to generate an intermediate image; estimate one or more scatter correction factors (SCFs) from the intermediate image; and reconstruct the emission imaging data corrected with the estimated SCFs to generate a reconstructed image. The second energy passband has a center energy that is at higher energy than the center energy of the acquisition energy passband, but still, covering the 511 keV photopeak.

In another disclosed aspect, an imaging system includes a positron emission tomography (PET) image acquisition device. At least one electronic processor is programmed to: receiving PET imaging data from an image acquisition device wherein the PET imaging data has been filtered using an acquisition energy passband; generating filtered imaging data by filtering the PET imaging data with a second energy passband that is narrower than an acquisition energy passband; reconstructing the filtered imaging data to generate an intermediate image; estimating one or more scatter correction factors (SCFs) from the intermediate image; and reconstructing the emission imaging data corrected with the estimated SCFs to generate a reconstructed image. The second energy passband has a center energy that is greater than that of a standard first energy passband but still, typically inclusive of 511 keV value, with, in some examples, a lower cutoff energy in the range 490-515 keV inclusive and an upper cutoff energy in the range 590-630 keV inclusive.

One advantage resides in providing reconstructed images with a lower scatter fraction.

Another advantage resides in providing reconstructed images for estimating scatter correction factors that are less affected by scattering content.

Another advantage resides in providing reconstructed images with reduced scattering content using more efficient reconstruction processing, which in some embodiments employs a single pass comprising a single scatter correction factor (SCF) simulation followed by a single (optionally iterative) PET image reconstruction using those SCFs.

Another advantage resides in simulating SCFs using a reduced amount of imaging data for faster reconstruction of emission estimate image used for scatter simulation.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the invention.

DETAILED DESCRIPTION

Figure 1:
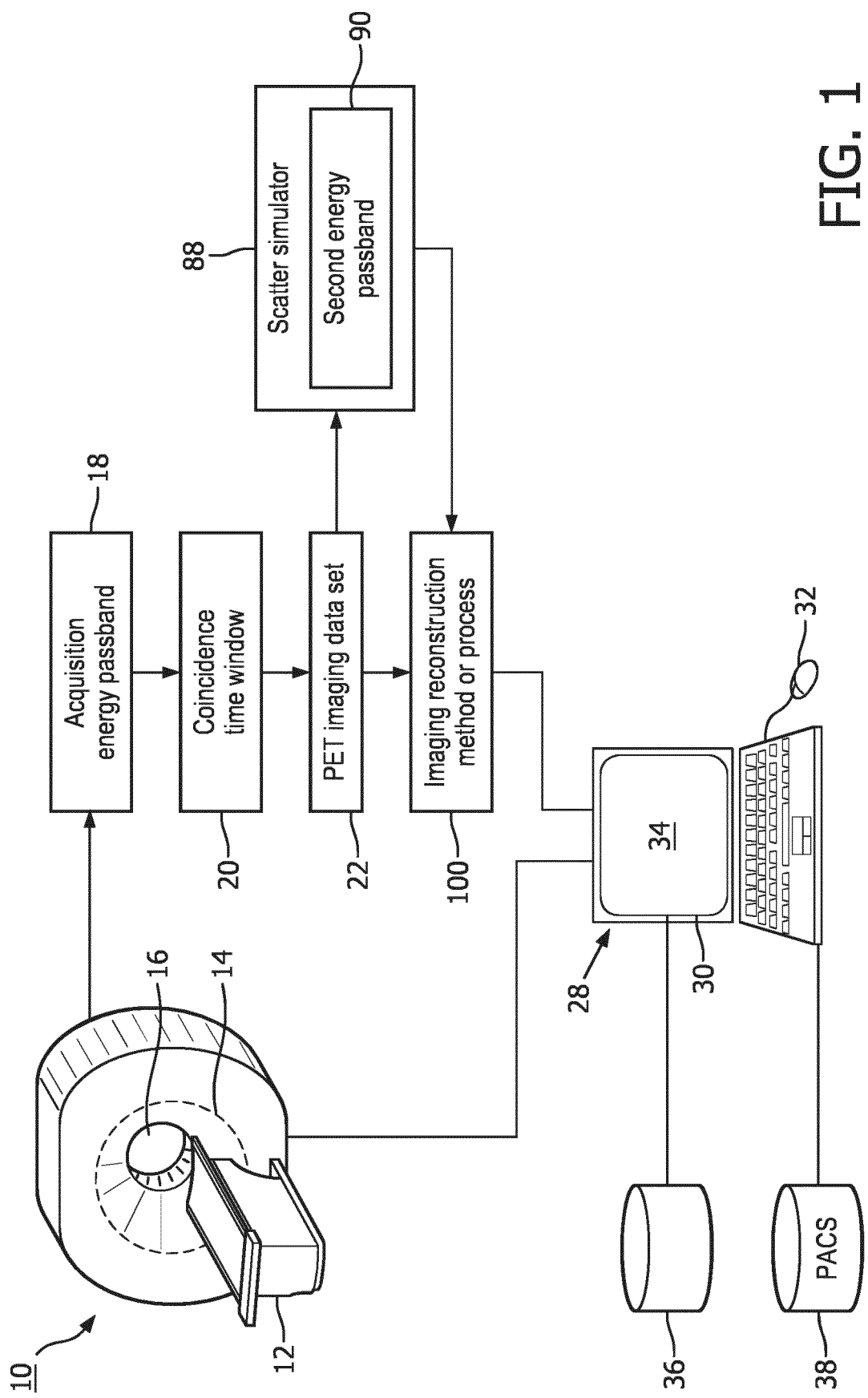
FIG. 1 diagrammatically shows image reconstruction system according to one aspect.

Given a reconstructed emission image, estimation of the scatter probabilities for various lines of response (LORs) is straightforward using known techniques such as single scatter simulation (SSS) processing. However, there is a "chicken-and-egg" problem—the reconstructed emission image includes scatter, and the scatter probabilities for the LORs are estimated from the reconstructed image that includes scatter. This can lead to systematic errors.

The usual solution for this problem is to operate iteratively: perform an initial reconstruction, estimate the scatter correction factors (SCFs) using the reconstructed image, then apply those SCFs to correct the original sinogram for scatter and repeat one or more times, with the expectation that successive iterations will improve the SCF estimation. This approach has difficulties: it is computationally expensive to perform the repeated image reconstructions; and the optimization is empirical and does not have a principled basis.

In embodiments disclosed herein, narrow energy window filtering is used to produce data with less scatter content which is reconstructed and used for the SCF estimation. It is to be understood that the collected list mode data are already energy window filtered, but using a broader energy window usually chosen on the basis of the energy resolution of the PET detectors. This broad initial energy window is usually about ±10-20% of the 511 keV energy, e.g. on the order of 450-615 keV in some commercial PET imaging devices.

By contrast, the narrow energy window is a narrower window that excludes a greater portion of the scatter events. The scatter events are typically inelastic, meaning that the scattered gamma rays usually lose energy; hence, as recognized herein the scatter events are generally at energies below the 511 keV defined by the physics of the electron-positron annihilation process. Thus, in one illustrative embodiment the narrow energy window is 510-615 keV, or more generally is asymmetric respective to the 511 keV line and shifted to higher energy versus a window that was symmetric about 511 keV.

The benefits of using the narrow energy window filtering are numerous. First, by preferentially removing scatter events, a total scatter fraction (i.e., a ratio of scattered events to total detected) is lower. Therefore, the reconstructed image used for estimating the SCFs is much less affected by scattering. The reconstructed image may be of higher variance due to reduced data statistics and/or coarser resolution can be employed to reduce the variance and speed up the reconstruction, but scatter estimation is only weakly affected by fine high frequency image details, and these factors are more than counterbalanced by the reduced scatter content in the narrow energy window filtered data. A further benefit is that the reduced amount of data provides for faster list-mode reconstruction simply because there is less data to process.

Another aspect is to employ time-of-flight (TOF) image reconstruction of the narrow energy window filtered data. The TOF reconstruction at least partially offsets the reduced image quality introduced by the removed data, as well as it further reduces the impact of scattered events due to additional spatial information dependency provided by TOF.

In another variant embodiment, the choice of narrow energy window may be made dependent on factors such as patient size (a heavier patient has more scatter and hence may justify using a narrower energy window) and direction (the energy window may be made directionally dependent to account for the wider girth of a typical patient in some directions compared with other directions). The amount of data statistics available also matters. In some examples, for high activity/longer acquisition durations when plenty of data are available, the second energy window may be further narrowed to further reduce the reconstruction speed for the preliminary emission estimate as well as further reduce the scatter fraction.

Another aspect is the use in some embodiments of a single pass, that is, reconstructing the narrow energy window filtered data and performing SCF estimation, then applying the SCFs and reconstructing the image, without a second or further iteration to refine the initial SCF estimation.

With reference to FIG. 1, an illustrative positron emission tomography (PET) imaging system 10 is shown. As shown in FIG. 1, the system 10 includes a PET acquisition device or scanner 12. The PET acquisition device 12 includes one or more rings of PET detectors 14 arranged to collect PET imaging data from a patient disposed in an examination region 16. The PET scanner 12 may, in general, be a conventional PET scanner or may have time-of-flight (TOF) localization capability. The PET imaging device employs digital or analog passband filtering with an acquisition energy passband 18 designed to detect 511 keV gamma rays. The acquisition energy passband 18 is usually chosen on the basis of the energy resolution of the PET detectors 14, e.g. a window extending about ±10-20% below/above the 511 keV energy. As a non-limiting illustrative example, in some embodiments the acquisition energy passband 18 is 450-615 keV. It will be appreciated that the acquisition energy passband 18 is sufficiently broad to pass a substantial fraction of 511 keV gamma rays. In some examples, the acquisition energy passband 18 is selected based on a system energy resolution (e.g., full width half maximum (FWHM)). For example, if an energy window of +−FWHM around 511 keV for the acquisition energy passband 18, more than 98% of the 511 keV photons are collected. In some instances, an upper cutoff greater than 511+FWHM is used to include more (e.g., <1% in theory) events.

The PET scanner 12 further employs coincidence detection using a coincidence time window 20 to detect coincident 511 keV gamma rays. This reflects the expectation that positrons emitted by the radiopharmaceutical administered to the patient for PET imaging annihilate with electrons, with each positron-electron annihilation event emitting two oppositely directed 511 keV gamma rays. Thus, a PET detection event corresponds to a pair of 511 keV gamma ray detection events that are simultaneous insofar as they are within the coincidence time window 20 of one another. The two coincident detection events define a line of response (LOR) connecting the two detection events. Optionally, each PET detection event further has time-of-flight (TOF) localization along the LOR based on the time difference (if any, within the coincidence time window 20) between the two detection events. The thusly defined coincident 511 keV gamma ray detection pair events (with optional TOF localization) define a PET imaging data set 22. It may be noted that the energy filtering using the acquisition energy window 18 and the coincidence detection using the coincidence time window 20, as well as the TOF localization if employed, may be implemented in various way, e.g. by tile- and/or module-level analog, digital, or hybrid electronics of the PET detectors 14, and/or by off-gantry electronics in the form of analog-to-digital circuitry, microprocessor or other computing hardware, and/or so forth, as is known in the art.

It may also be noted that the disclosed scatter correction approaches may be employed in conjunction with other types of emission imaging, such as single photon emission computed tomography (SPECT) imaging.

The system 10 also includes a computer or workstation or other electronic data processing device 28 with typical components, such as at least one electronic processor 30, at least one user input device (e.g., a mouse, a keyboard, a trackball, and/or the like) 32, and a display device 34. In some embodiments, the display device 34 can be a separate component from the computer 28. The workstation 28 can also include one or more databases 36 (stored in a non-transitory storage medium such as RAM or ROM, a magnetic disk, or so forth), and/or the workstation can be in electronic communication with one or more databases 38 (e.g., an electronic medical record (EMR) database, a picture archiving and communication system (PACS) database, and the like). As described herein the database 38 is a PACS database.

The at least one electronic processor 30 is operatively connected with a non-transitory storage medium (not shown) that stores instructions which are readable and executable by the at least one electronic processor 30 to perform disclosed operations including performing a scatter simulation 88 which as disclosed herein operates on data selected by bandpass filtering using a second energy passband 90 which is narrower than the acquisition energy passband 18 used to identify (nominally) 511 keV gamma rays by reducing the scatter fraction during collection of the PET imaging data 22; and performing an image reconstruction method or process 100. The second energy passband 90 can be selected based on data statistics of the PET imaging data 22 (which can be generated to process the imaging data more quickly). In some examples, images can be reconstructed using PET imaging data 22 filtered with the second energy passband 90. The non-transitory storage medium may, for example, comprise a hard disk drive, RAID, or other magnetic storage medium; a solid state drive, flash drive, electronically erasable read-only memory (EEROM) or other electronic memory; an optical disk or other optical storage; various combinations thereof; or so forth. In some examples, the image reconstruction method 100 may be performed by cloud processing.

Figure 2:
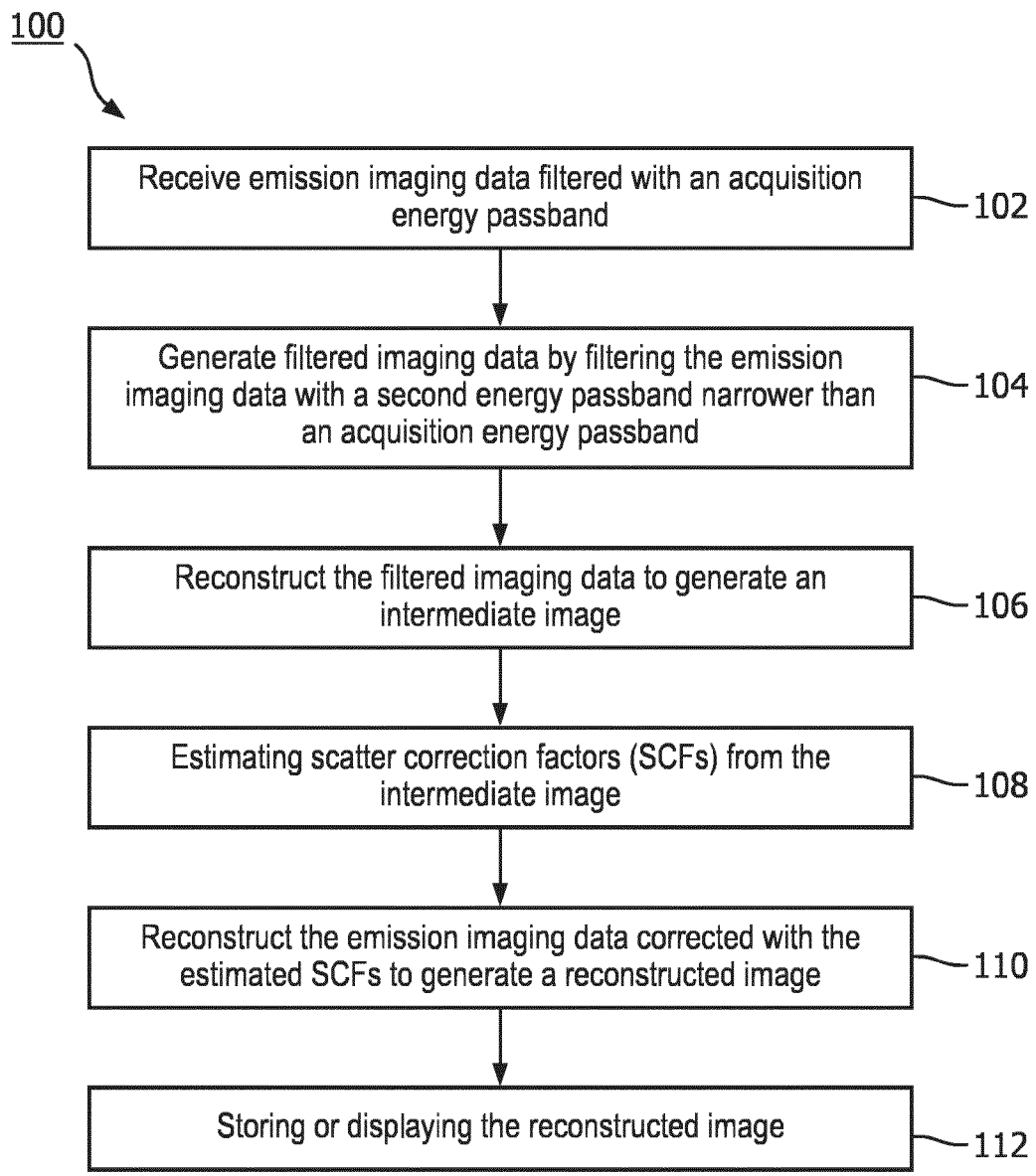
FIG. 2 shows an exemplary flow chart operation of the system of FIG. 1.

With reference to FIG. 2, an illustrative embodiment of the scatter simulation 88 and image reconstruction 100 is diagrammatically shown as a flowchart. At 102, the at least one electronic processor 30 is programmed to receive emission imaging data 22 from the PET device 12. The emission imaging data (i.e., PET list mode imaging data in the illustrative embodiment, or in other contemplated embodiments SPECT imaging data) is filtered using the acquisition energy passband 18 centered around 511 keV (or around the single-photon emission energy in the case of SPECT). For example, the acquisition energy passband can be about ±10-20% of the 511 keV energy, e.g. on the order of 450-615 keV in some embodiments.

At 104, filtered imaging data is generated by filtering the emission imaging data with the second energy passband 90 that is narrower than an acquisition energy passband 18. This narrower energy window including 511 keV has the effect of excluding more scatter events than does the acquisition energy passband 18.

In some embodiments, the second energy passband 90 is asymmetric respective to the 511 keV energy, with its center energy located above 511 keV and its lower cutoff energy close to 511 keV but still inclusive. For example, in a non-limiting illustrative example, the second energy passband 90 has a center energy that is greater than 511 keV, and has a lower cutoff energy in the range 490-515 keV inclusive and an upper cutoff energy in the range 590-630 keV inclusive. The rationale behind such embodiments is that scatter events are typically inelastic events. In an inelastic event, energy is gained or lost. In the case of a 511 keV gamma ray being scattered off electrons of an atom or the like, it is most likely the high energy (511 keV) gamma ray will lose energy. Thus, 511 keV gamma rays that undergo scatter are more likely to have energies less than 511 keV due to energy loss in one or more scattering events, rather than having energy greater than 511 keV. Thus, having the lower cutoff energy of the second energy passband 90 positioned at 511 keV or slightly below 511 keV (e.g. in the range 490-515 keV inclusive in the illustrative example) excludes more scatter events than would an energy passband of the same width but centered at 511 keV. In another non-limiting illustrative example, the second energy passband has a lower cutoff energy within 5% inclusive of 511 keV. In some examples, modeling of the acquisition energy passband 18 and/or the second energy passband 90 can be performed using a Gaussian distribution.

The second energy passband 90 can also be selected based on other factors, such as patient size, patient girth, or direction of the LOR. In one example, a heavier patient has more scatter and hence may justify using a narrower energy window. In another example, the width of the second energy passband may be made directionally dependent to account for the wider girth of a typical patient in some directions compared with other directions. Thus, events whose LORs are approximately parallel with the wider girth of the patient may be filtered with a second energy passband that is different than is used for filtering events whose LORs are approximately transverse to the wider girth of the patient. Since the bandpass filtering using the second energy passband 90 is performed prior to image reconstruction, the directional dependence of the second energy passband 90 is suitably chosen based on the a priori known position of the patient, e.g. a patient lying prone or supine will have the wider girth in the horizontal direction. If a directionally dependent second energy passband 90 is employed, then appropriate sensitivity normalization factors can be used during image reconstruction.

At 106, the filtered imaging data is reconstructed to generate an intermediate image. In some examples, the reconstruction can employ TOF image reconstruction to improve the quality of the image. Advantageously, the filtered imaging data (i.e., having fewer list mode events) can be reconstructed more quickly while having a smaller amount of scatter content, as compared with reconstructing the entire PET imaging data set 22. Using the narrower energy window 90, more scatter events are excluded. At the same time, some amount of true LOR events are also excluded because of the imperfect energy resolution (which can be around ~10-15% at 511 keV), which means the intermediate image includes fewer true LOR events in the data to be reconstructed.

At 108, one or more scatter correction factors (SCFs) are estimated from the intermediate image, for example using single scatter simulation (SSS), full Monte Carlo or another scatter estimation technique for the PET imaging data 22 (received at 102). In one particular implementation, the estimation can be performed using Monte Carlo simulation to determine a scaling factor by comparing to measured sinograms data and then scale the scatter component to achieve the accurate quantification.

At 110, the emission imaging data 22 are reconstructed by the image reconstruction 100 (see FIG. 1) using an iterative image reconstruction such as maximum likelihood-expectation maximization (ML-EM), ordered subset expectation maximization (OSEM), or another image reconstruction algorithm, and including scatter correction performed with the estimated SCFs, to generate a reconstructed image. In some examples, the reconstruction can employ TOF image reconstruction to improve the quality of the image. In the image reconstruction 110 (unlike the image reconstruction 106 performed as part of the scatter simulation 104, 106, 108) the full PET imaging dataset 22 is reconstructed. However, as just described, the SCFs used in the image reconstruction 110 were generated by performing the scatter simulation on the image reconstructed in the step 106 which used only the imaging data filtered by the second energy passband 90.

At 112, the reconstructed image output by the image reconstruction 110 can be displayed on the display device 24, saved in the PACS database 28, or both. To do so, the at least one electronic processor 20 is programmed to control the display device 24 to display the reconstructed image, or control the PACS database 28 to store the reconstructed image. Advantageously, the image reconstruction method 100 may be performed a single time, in order to more quickly generate the reconstructed image more quickly while reducing the amount of scatter in the reconstructed image.

With reference back to FIG. 1, the scatter simulator 88 and the image reconstruction 100 are illustrated as separate components. The scatter simulator 88 performs the operations 104, 106, 108 of the process of FIG. 2, while the image reconstruction 100 performs the image reconstruction step 110 of the process of FIG. 2. However, the two components 88, 100 of FIG. 1 may be variously combined by leveraging common processing subroutines, functions, modules, or the like. For example, the two image reconstruction steps 106, 110 may use the same image reconstruction algorithm, or alternatively may use different reconstruction algorithms (or may use the same reconstruction algorithm with different parameters). For example, the image reconstruction 110 of the full PET imaging data set 22 may use OSEM to efficiently handle the larger data set 22 by partitioning into (ordered) subsets; whereas the image reconstruction 106 operating on the smaller data set output by the filtering 104 may optionally use ML-EM or another imaging reconstruction technique that does not partition the data into subsets.

Figure 3:
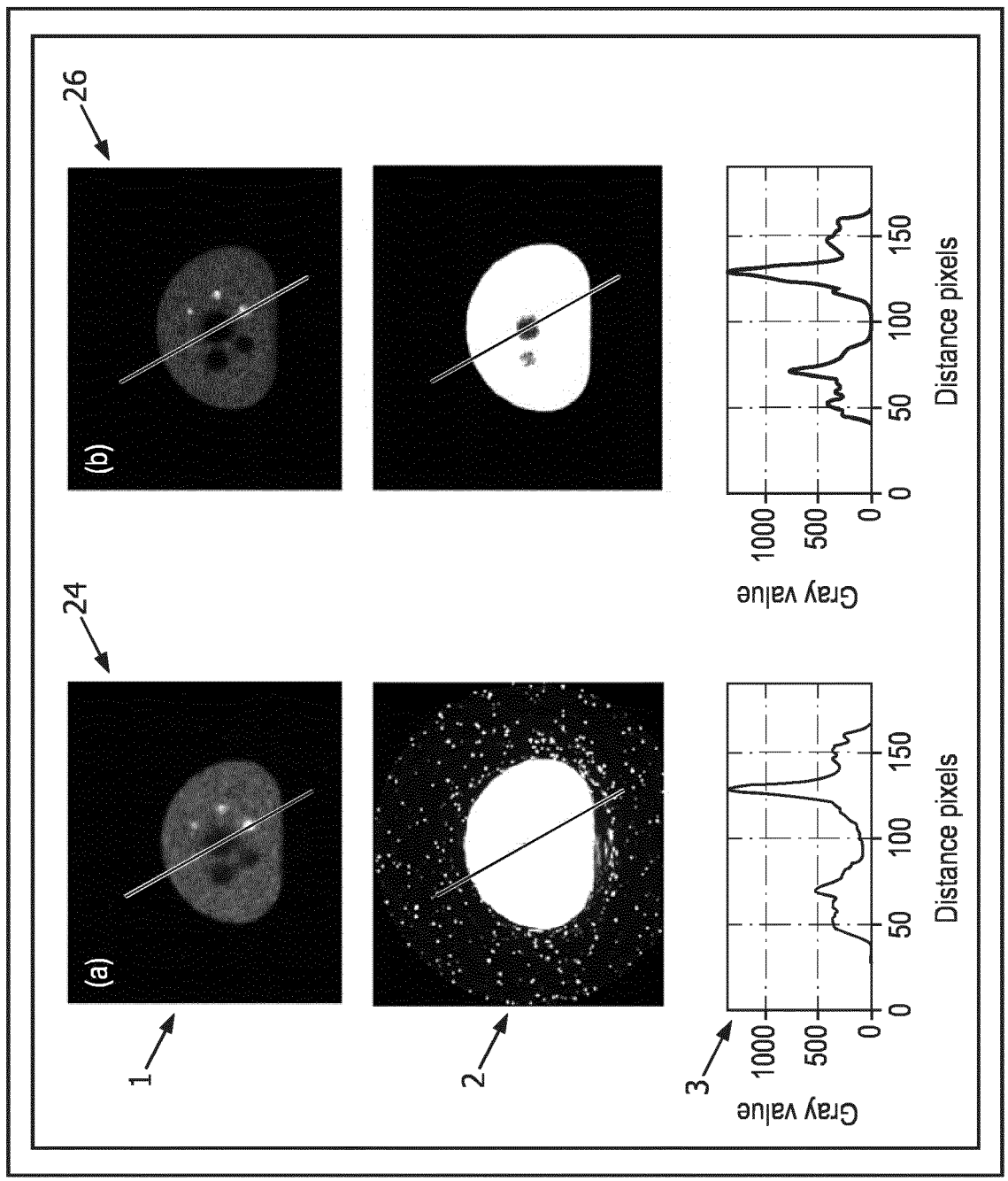
FIG. 3 illustratively shows images reconstructed by of the system of FIG. 1.

FIG. 3 shows an example of the display device 34 displaying a comparison of a typical reconstructed image 24 (i.e., reconstructed with non-TOF data and using only the acquisition energy passband 18) and a reconstructed image 26 generated by the image reconstruction method 100 (i.e., using the acquisition energy passband 18 and the second energy passband 90). The reconstructed image 26 has a higher cold contrast (shown in row 1) and background cleanliness (shown in row 2) compared to the reconstructed image 24 due to the reconstructed image 26 being filtered with the second energy passband 90 and using TOF. The third row labeled row 3 shows a corresponding profile drawn through the centers of the reconstructed images 24 and 26. In this example, the reconstructed image 26 was reconstructed using 96-104% of 511 keV as the second (narrow) energy passband.

The disclosure has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A non-transitory storage medium storing instructions readable and executable by an electronic processor, wherein the electronic processor performs an image reconstruction method comprising:
   receiving emission imaging data from an image acquisition device wherein the emission imaging data has been filtered using an acquisition energy passband;
   generating filtered imaging data by filtering the emission imaging data with a second energy passband that is narrower than an acquisition energy passband;
   reconstructing the filtered imaging data to generate an intermediate image;
   estimating one or more scatter correction factors (SCFs) from the intermediate image; and
   reconstructing the emission imaging data corrected with the estimated SCFs to generate a reconstructed image.

2. The non-transitory storage medium of claim 1, wherein the emission imaging data is positron emission tomography (PET) imaging data and the second energy passband has a center energy that is greater than, and inclusive of, 511 keV.

3. The non-transitory storage medium of claim 2, wherein the second energy passb and has a lower cutoff energy in the range 490-515 keV inclusive and an upper cutoff energy in the range 590-630 keV inclusive.

4. The non-transitory storage medium of claim 1, wherein the second energy passband has a center energy that is at higher energy than the center energy of the acquisition energy passband.

5. The non-transitory storage medium of claim 4, wherein the second energy passband has a lower cutoff energy within 5% inclusive of the center energy of the acquisition energy passband.

6. The non-transitory storage medium of claim 5, wherein the method is performed a single time to generate the at least one reconstructed image.

7. The non-transitory storage medium of claim 1, wherein the method further includes;
   selecting the second energy passband based on patient size.

8. The non-transitory storage medium of claim 7, wherein the selecting the second energy passband based on patient size includes:
   selecting the second energy passband on the basis of patient girth.

9. The non-transitory storage medium of claim 8, wherein the selecting the second energy passband based on patient size includes:
   selecting a direction of the second energy passband based on a known position of the patient prior to reconstruction of the filtered imaging data.

10. The non-transitory storage medium of claim 9, wherein the second energy passband has a width that is dependent on direction of the emission imaging data being filtered.

11. The non-transitory storage medium of claim 1, wherein the emission imaging data is positron emission tomography (PET) imaging data and the reconstructing of at least one of the PET imaging data corrected with the estimated SCFs and the intermediate image employs time-of-flight (TOF) image reconstruction.

12. The non-transitory storage medium of claim 1, wherein the method further includes at least one of:
   displaying the reconstructed image on a display device; and storing the reconstructed image in a Picture Archiving and Communication System (PACS) database.

13. An imaging system, comprising:
an image acquisition device; and
at least one electronic processor programmed to:
receive emission imaging data from the image acquisition device wherein the emission imaging data has been filtered using an acquisition energy passband;
generate filtered imaging data by filtering the emission imaging data with a second energy passband that is narrower than an acquisition energy passband;
reconstruct the filtered imaging data to generate an intermediate image;
estimate one or more scatter correction factors (SCFs) from the intermediate image; and
reconstruct the emission imaging data corrected with the estimated SCFs to generate a reconstructed image;
wherein the second energy passband has a center energy that is at higher energy than the center energy of the acquisition energy passband.

14. The imaging system of claim 13, wherein the emission imaging data is positron emission tomography (PET) imaging data and the second energy passband has a center energy that is greater than 511 keV, a lower cutoff energy in the range 490-515 keV inclusive and an upper cutoff energy in the range 590-630 keV inclusive.

15. The imaging system of claim 14, wherein the second energy passband has a lower cutoff energy within 5% inclusive of the center energy of the acquisition energy passband.

16. The imaging system of claim 13, wherein the at least one electronic processor is further programmed to:
select the second energy passband based on patient size.

17. The imaging system of claim 13, wherein the at least one electronic processor is further programmed to:
select the second energy passband having a width that is dependent on direction of the emission imaging data being filtered.

18. The imaging system of claim 17, wherein the at least one electronic processor is further programmed to:
select the second energy passband on the basis of patient girth.

19. The imaging system of claim 18, wherein the at least one electronic processor (30) is further programmed to:
select a direction of the second energy passband based on a known position of the patient prior to reconstruction of the filtered imaging data.

20. The imaging system of claim 13, wherein the emission imaging data is positron emission tomography (PET) imaging data and the at least one electronic processor is further programmed to:
reconstruct at least one of the PET imaging data corrected with the estimated SCFs and the intermediate image employing time-of-flight (TOF) image reconstruction.

21. An imaging system, comprising:
a positron emission tomography (PET) image acquisition device; and
at least one electronic processor programmed to:
receiving PET imaging data from an image acquisition device wherein the PET imaging data has been filtered using an acquisition energy passband;
generating filtered imaging data by filtering the PET imaging data with a second energy passband that is narrower than an acquisition energy passband;
reconstructing the filtered imaging data to generate an intermediate image;
estimating one or more scatter correction factors (SCFs) from the intermediate image; and
reconstructing the emission imaging data corrected with the estimated SCFs to generate a reconstructed image;
wherein the second energy passb and has a center energy that is greater than 511 keV, a lower cutoff energy in the range 490-515 keV inclusive and an upper cutoff energy in the range 590-630 keV inclusive.

22. The imaging system of claim 21, wherein the second energy passband has a center energy that is at higher energy than the center energy of the acquisition energy passband, and a lower cutoff energy within 5% inclusive of the center energy of the acquisition energy passband.

23. The imaging system of claim 22, wherein the at least one electronic processor is further programmed to at least one of
select the second energy passband based on patient size; and
select the second energy passband having a width that is dependent on direction of the emission imaging data being filtered.

24. The imaging system of claim 21, wherein the at least one electronic processor is further programmed to:
reconstruct at least one of the PET imaging data corrected with the estimated SCFs and the intermediate image employing time-of-flight (TOF) image reconstruction.

25. The non-transitory storage medium of claim 21, wherein the at least one electronic processor is further programmed to:
control a display device to display the reconstructed image; and
store the reconstructed image in a Picture Archiving and Communication System (PACS) database.

* * * * *